United States Patent
Schobitz Twele et al.

(10) Patent No.: US 8,062,633 B2
(45) Date of Patent: Nov. 22, 2011

(54) **SURFACE SANITIZER FOR THE FOOD INDUSTRY BASED ON THREE NEW LACTIC ACID BACTERIA THAT HAVE ANTAGONISTIC ACTION AGAINST *LISTERIA MONOCYTOGENES*, THE MICROORGANISM THAT CAUSES LISTERIOSIS IN HUMANS**

(75) Inventors: Renate Paula Schobitz Twele, Valdivia (CL); Luigi Ciampi Panno, Valdivia (CL); Marcia Enriqueta Costa Lobo, Valdivia (CL); Carmen Susana Brito Contreras, Valdivia (CL); Juan Ricardo Fuentes Perez, Valdivia (CL); Mariela Horzella Rademacher, Valdivia (CL); Yanina Iveth Nahuelquin Rios, Valdivia (CL); Cristina del Carmen Vergara Hinostroza, Valdivia (CL)

(73) Assignee: Universidad Austral de Chile, Valdivia (CL)

( * ) Notice: Subject to any disclaimer, the term of this patent is extended or adjusted under 35 U.S.C. 154(b) by 0 days.

(21) Appl. No.: 12/714,220

(22) Filed: Feb. 26, 2010

(65) Prior Publication Data

US 2010/0239561 A1   Sep. 23, 2010

Related U.S. Application Data

(60) Provisional application No. 61/162,811, filed on Mar. 24, 2009.

(30) Foreign Application Priority Data

Mar. 20, 2009   (CL) ..................................... 688-2009
Mar. 20, 2009   (CL) ..................................... 689-2009
Nov. 30, 2009   (CL) ................................... 2147-2009

(51) Int. Cl.
*A01N 63/00*   (2006.01)
*A01N 65/00*   (2006.01)
(52) U.S. Cl. ...................... 424/93.1; 424/93.3; 424/93.4
(58) Field of Classification Search ........................ None
See application file for complete search history.

(56) References Cited

U.S. PATENT DOCUMENTS 5,451,369 A   9/1995   Daeschel et al.
6,054,163 A   4/2000   Wettenhall et al.

FOREIGN PATENT DOCUMENTS

WO   WO 2007/106993   9/2007

OTHER PUBLICATIONS

Costerton et al. "Bacterial Biofilms: A Common Cause of Persistent Infections." *Science*. vol. 284. 1999. pp. 1318-1322.
Wiedemann et al. "Specific Binding of Nisin to the Peptidoglycan Precursor Lipid II Combines Por Formation and Inhibition of Cell Wall Biosynthesis for Potent Antibiotic Activity." *Journal of Biological Chemistry*. vol. 276. No. 1. 2001. pp. 1772-1779.
Chmielewski et al. "Biofilm Formation and Control in Food Processing Facilities." *Comprehensive Reviews in Food Science and Food Safety*. vol. 2. 2003. pp. 22-32.
Pan et al. "Resistance of *Listeria monocytogens* Biofilms to Sanitizing Agents in Simulated Food Processing Environment." *Applied and Environmental Microbiology*. vol. 72. No. 12. 2006. pp. 7711-7717.
Jeyasekaran et al. "Effect of Sanitizers on *Listeria* Biofilm on Contact Surfaces." *Asian Fisheries Science*. vol. 13. 2000. pp. 209-213.
Guilbaud et al. "Quantative Detection of *Listeria monocytogens* in Biofilms by Real-Time PCR." *Applied and Environmental Microbiology*. vol. 71. No. 4. 2005. pp. 2190-2194.

*Primary Examiner* — Albert Navarro
(74) *Attorney, Agent, or Firm* — Merchant & Gould P.C.

(57) ABSTRACT

The present invention relates to a formulation useful to control *Listeria monocytogenes* that comprises three new lactic acid bacteria, namely *Carnobacterium maltaromaticum* ATCC® PTA-9380, *C. maltaromaticum* ATCC® PTA-9381 and *Enterococcus mundtii* ATCC® PTA-9382 together with the bacteriocin nisin. This formulation is obtained from Inactivated Fermentates (IF) of these strains plus nisin and is designed to be used in the food industry. This formulation is used as an agent with tested antagonistic and bactericidal action against the pathogen *Listeria monocytogenes*, the microorganism that causes listeriosis, a food-borne disease, in humans. Based on this formulation, 2 surface sanitizing products can be obtained, a liquid and a solid. Both surface sanitizers can be applied to sanitize equipments, devices, working surfaces, gutters and drainages, especially in the food industry.

18 Claims, 3 Drawing Sheets

SURFACE SANITIZER FOR THE FOOD INDUSTRY BASED ON THREE NEW LACTIC ACID BACTERIA THAT HAVE ANTAGONISTIC ACTION AGAINST *LISTERIA MONOCYTOGENES*, THE MICROORGANISM THAT CAUSES LISTERIOSIS IN HUMANS

This application claims benefit of Ser. No. 0688-2009, filed 20 Mar. 2009 in Chile, Ser. No. 0689-2009, filed 20 Mar. 2009 in Chile, Ser. No. 2147-2009, filed 30 Nov. 2009 in Chile and U.S. Ser. No. 61/162,811, filed 24 Mar. 2009 and which applications are incorporated herein by reference. To the extent appropriate, a claim of priority is made to each of the above disclosed applications.

BACKGROUND

The present invention relates to a formulation useful to control *Listeria monocytogenes* that comprises three new lactic acid bacteria, namely *Carnobacterium maltaromaticum* ATCC® PTA-9380, *C. maltaromaticum* ATCC® PTA-9381 and *Enterococcus mundtii* ATCC® PTA-9382 together with the bacteriocin nisin. This formulation is obtained from Inactivated Fermentates (IF) of these strains plus nisin and is designed to be used in the food industry. This formulation is used as an agent with tested antagonistic and bactericidal action against the pathogen *Listeria monocytogenes*, the microorganism that causes listeriosis, a food-borne disease, in humans. Based on this formulation, 2 surface sanitizing products can be obtained, a liquid and a solid. Both surface sanitizers can be applied to sanitize equipments, devices, working surfaces, gutters and drainages, especially in the food industry.

Technical Problem Addressed

One of the main and constant concern in the food industry is the survival of pathogenic microorganisms prevailing in processed food, which cause intoxications and diseases in humans. This is the case of the bacterium *L. monocytogenes*, the pathogen that causes listeriosis. It has been broadly demonstrated that listeriosis is a food-borne disease and its higher risk target groups are pregnant women, neonates and immuno-compromised adults. The presence of *L. monocytogenes* is particularly risky in "ready-to-eat food", which are not subjected to any heat treatment before consumption. This represents a serious problem for consumer's health and an economical drawback for the industry due to the costs of withdrawal of products from the market when a suspected contaminated food is confirmed.

In Chile, listeriosis cases increased fourfold during 2008 only in Santiago, causing the death of five people. The Health Ministry of Chile informed on Dec. 30, 2008 that only in the Metropolitan Area 115 positive cases were reported associated to *L. monocytogenes* in the different public and private health institutions of the Metropolitan Area. To May 2009, 27 cases have been reported with a total toll of seven deceased victims. This reality makes it imperative to develop new tools that provide food safety for the population that consumes dairy foods, soft cheeses, raw meats, raw fish, cold smoked salmon, sausages and luncheon meats.

The products currently used in the industry for the control, prevention and elimination of *L. monocytogenes* do not ensure elimination or destruction of microorganisms during the stages of processing of raw materials and transport and delivery of the product to destination markets. Food industry uses chemical products such as alcohol, chlorine dioxide, quaternary ammonium compounds, peracetic acid, sodium hypochlorite and the like for cleaning and sanitization. However, these products are not effective to eliminate *L. monocytogenes*, particularly when this agent is immersed in a "biofilm" formed by microorganism communities that grow embedded in a polysaccharide matrix and adhered to an inert surface or a living tissue (Costerton, J. Stewart, P. and Greenberg, E. 1999. Bacterial biofilms: a common cause of persistent infections. Science 284: 1318-1322). These biofilms are located usually in industrial working surfaces and processed foods can be contaminated from these sources. These biofilms are formed by exopolysaccharides secreted by bacteria themselves, which act as a guard against sanitizer action, since they hinder the penetration of sanitizers and allows *L. monocytogenes* to survive. The sanitizer of this invention has the characteristic of inhibiting or destroying *L. monocytogenes* inside biofilms.

In general, the products used in the industry are described as corrosive and irritant and/or having cumulative effects in humans, including carcinogenic effects, and so companies have to exert a permanent control of used dosages. Damage to the environment caused by these agents through discharge in liquid industrial residues from food industries is also a concern. Failure of these sanitizers to destroy *L. monocytogenes* has been evidently assessed by a notorious increase in listeriosis outbreak cases.

With this in mind, the possibility of offering the industry a biological surface sanitizing product is an opportunity given the high demand of the food processing industries for products that are not harmful or have undesired side effects on food products. Moreover, it is worth mentioning that the product of this invention is environmentally-friendly and innocuous for humans, and is also able to inhibit *L. monocytogenes* even inside biofilms.

SUMMARY

*L. monocytogenes*, the pathogen causing listeriosis in humans, is a microorganism that is very resistant to adverse environmental factors. It can be found in a wide variety of plant- or animal-based foods, both fresh and processed. It has been found in vegetables, milk, cheese, beef meat, pork meat, fowl meat, smoked and fermented sausages and meats, raw shellfish and smoked fish.

This pathogen can grow at a pH ranging from 4.4 to 9.2; at temperatures ranging from 3.0 to 45° C., and at a water activity ($A_w$) as low as 0.92. Moreover, it is able to grow in the presence of high concentrations of salts (NaCl), up to 10%. In other words, the pathogen can survive in acid or basic, refrigerated, dehydrated or salted foods.

*L. monocytogenes* is a facultative intracellular agent. Listeriosis is associated to meningoencephalitis, septicemia and abortion in humans. This is especially true in high risk individuals, such as: pregnant women, newborns, the elderly and immunocompromised patients.

Human listeriosis belongs to the group of food-borne diseases (FBD), food being the main entrance vehicle of *L. monocytogenes* into the human body. This disease is considered a food-borne toxiinfection with low incidence but high lethality, with symptoms such as: Fever, gastrointestinal alterations or muscular pain. The infection extends through the nervous system, which originates other symptoms such as equilibrium loss, headache or confusion, and can end up in septicemia, meningitis or abortion. The infection can present itself as individual cases or as outbreaks, which can evolve into much more severe cases.

As a consequence of its high mortality rates, listeriosis is placed among the most frequent causes of death due to consumption of contaminated food. The responsible microorganism, *L. monocytogenes*, is resistant to traditional inhibition methods.

Ready-to-eat food must be manipulated under stringent hygiene standards and conserved at refrigerated temperatures. Such food includes, for example, soft matured cheeses, fermented raw meat sausages, ice creams, raw vegetables, raw and cooked chicken meat, raw beef, and raw and smoked fish and shellfish.

At the authority and food industry level, the concern to avoid the propagation of this disease has increased in the last years. It is usual to find *Listeria* in raw fish, since it is a usual member of fish intestinal microflora. In smoked salmon production, the microorganism usually contaminates fish during evisceration and in subsequent cleaning, filleting and salting stages.

Total elimination of *L. monocytogenes* from the food industry environment is practically impossible, because the pathogen enters with raw materials and employees. Applying rigorous sanitary barriers at plant entrances help reducing *L. monocytogenes* presence, but the microorganism tends to remain in difficulty accessible places, such as drainages, gutters, water puddles on the floor, equipment and floors. Therefore, the option is to control the risk of presence in food and, consequently, its access to consumers. At the industrial level, in food processing, the growth of *L. monocytogenes* has to be monitored at each stage to avoid potentially hazardous levels.

In food, maximal accepted *L. monocytogenes* levels in the European Union are <100 CFU/g of final product (CFU: colony forming unit). FDA (Food and Drug Administration, USA) establishes zero tolerance in ready-to-eat products, while in Chile Sernapesca establishes a limit of <100 CFU/g of product.

One way to control the pathogen in the environment of food processing industries is using natural antagonistic microbiota and/or its products. This can be achieved by inoculating antagonistic bacterial strains in a culture medium, where they will produce substances that are antagonistic to *Listeria*.

Lactic acid bacteria (LAB) are considered as GRAS (generally recognized as safe) and have good biocontrolling properties, their main microbial antagonistic mechanisms being the competition for nutrients and the formation of lactic and acetic acids, with a consequent pH decrease. Moreover, they can produce peptides with antimicrobial properties known as bacteriocins.

Antimicrobial peptides have a bactericidal or bacteriostatic activity against other closely related species. This action has been observed more notoriously against a wide range of Gram-positive bacteria. In all cases, the producing cell exhibits specific immunity against the action of its specific bacteriocin.

Bacteriocin-producing strains can be clearly identified in a plate antagonism assay. In this assay, an indicator strain is cultured in a uniform lawn with drops of the extract containing the inhibitory substances are dropped on a lawn with the sensitive indicator organism. After incubation, inhibition areas can be observed in the lawn culture of the sensitive strain.

The interest in the study of bacteriocins has considerably increased in the last years, due to their potential use as a food safety factor. Many of these substances inhibit the growth of both pathogenic bacteria and food spoilage bacteria. This is a remarkable aspect, since these compounds can be used not only individually but also as a part of a barrier technology system where several agents are used to avoid bacterial growth instead of a single agent. This barrier system using several bacteriocins plus a commercial product has been patented for use in foods (Patent WO 2007/106993 A1). With this strategy, many aspects of the microbial growth process are simultaneously affected, thus achieving a synergic effect between them. The different bacteriocins can have different action mechanisms, which makes the antagonistic activity against the development of resistant cells more effective.

Humans have ingested bacteriocins for centuries. Many bacteriocin-producing LABs are used as acidifying and fermenting cultures in the dairy industry. LABs are generally recognized as safe (GRAS) by sanitary authorities. Therefore, the ingestion of bacteriocins in dosages naturally producible by LABs is safe for the consumers.

The bacteriocin mode of action is complex. In general, they act by destroying the integrity of the cytoplasm membrane through pore formation, which causes an efflux of small compounds or alters the proton motive force necessary for energy production and synthesis of proteins and nucleic acids. Bacteriocin monomers form pore-forming protein aggregates causing a consequent ion efflux (mainly potassium and magnesium), loss of the proton motive force, and efflux of ATP (adenosine-tri-phosphate) and amino acid. Consequently, macromolecule synthesis and energy production are abolished, thus causing cell death.

A known bacteriocin for the control of *L. monocytogenes* in food is nisin, which has the ability to inhibit sporulating microorganisms and also *L. monocytogenes*, but only for reduced periods. Nevertheless, as shown below in the examples, the formulation and the surface sanitizers of the present invention have a surprising effect due to the composition of the new LABs as well as their combined action with nisin.

Nisin is produced by *Lactococcus* lactis strains and inhibits a broad range of Gram-positive bacteria. These bacteriocins belong to the lantibiotics group (class I bacteriocins) and has a long history as food preservative (Wiedemann, Breukinks, Van Kraaij, Kuipers, Bierbaum, De Kruijff and Sahl. 2001. Specific binding of Nisin to the peptidoglycan precursor lipid II combines pore formation and inhibition of cell wall biosynthesis for potent antibiotic activity. Journal of Biological Chemistry 276 (1):1772-1779).

The formulation and surface sanitizers of the present invention are able to prevent the presence of or eliminate *L. monocytogenes* from working surfaces where these foods are processed and manipulated. Currently, these products are exposed to contamination with this pathogen in the entire production line. The organic sanitizing product is biologically based on the fact that LABs or their antagonistic products prevent the development and eliminate *L. monocytogenes* from working surfaces and any other place or environment where food is processed.

The novelty of this product is the applicability of LAB strains in the food industry as surface sanitizers obtained from inactivated fermentates (IF) of 3 LABs and also including the bacteriocin nisin. Preferably, LAB cultures are inactivated through a unique system referred to as Thermally Treated Fermentate (TTF). It is worth to mention that LABs used in this invention are native from Chile. They were isolated and evaluated in the laboratories of the Austral University of Chile (UACh) and were deposited at the ATCC® (American Type Culture Collection).

For the sanitary authority, *L. monocytogenes* is a "permanent threat" in the food production value chain, especially in ready-to-eat food. The products currently used to eliminate *L. monocytogenes* do not ensure a total sanitization during the stages of production and transport to destination markets.

Moreover, the application of chemical products is increasingly questioned because of their side effects on human health and the direct or indirect damage caused by their derivatives to the environment through discharges of liquid industrial residues.

A problem that has to be faced by the food industry in general is the ability of certain bacteria, and *L. monocytogenes* among them, to form biofilms.

These biofilms do not allow sanitizers to penetrate them, so *L. monocytogenes* can survive. An effective cleaning procedure must break or dissolve the extracellular polymeric substance matrix associated in the biofilm, to allow sanitizing agents to access viable cells (Chmielewski, R. and Frank, J. 2003. Biofilm formation and control in food processing facilities. Comprehensive Reviews in Food Science and Food Safety 2: 22-23).

Pan, Y., Breidt, F., and Kathariou, S. (2006. Resistance of *Listeria monocytogenes* Biofilms to Sanitizing Agents in a Simulated Food Processing Environment. Applied and Environmental Microbiology 72(12): 7711-7717) studied the resistance of *L. monocytogenes* in biofilms formed on stainless steel subjected to different sanitizing agents, such as hydrogen peroxide, quaternary ammonium compounds, chlorine derivatives and other products usually used in the food industry, observing as a result that *L. monocytogenes* counts in the biofilms decreased during the first week of treatment, but then increased again. The authors explain this resistance as due to the exopolysaccharide matrix inside which microorganisms are embedded, which hinders the penetration of the sanitizers. This illustrates the case of some usual commercial sanitizers. The work of Jeyasekaran, G. Karunasagar, I. and Karunasagar, I. (2000. Effect of Sanitizers on *Listeria* Biofilm on Contact Surfaces. Asian Fisheries Science 13: 209-213), demonstrates that washing and sanitizing processes with products such as chlorine derivatives in food industry surfaces do not eliminate *L. monocytogenes* biofilms but only reduces them, since chlorine is inactivated in the presence of organic matter.

The former situation is solved by using the liquid or solid surface sanitizers of this invention because the antagonistic substances therein are able to penetrate the formed biofilm. A *L. monocytogenes* biofilm as usually found in the food industry has a microbial population in the order of $10^2$ CFU/cm$^2$ (Gulba, M., de Coppet, P, Bourion, F., Rachman, C., Prevost, H., and Dousset, X., 2005. Quantitative Detection of *Listeria monocytogenes* in Biofilms by Real-Time PCR. Applied and Environmental Microbiology 71(4): 2190-2194), a population that could be completely eliminated 24 hours after applying the surface sanitizer of the invention, since in this time the population is reduced more than 2 log cycles in comparison to the initial count. Furthermore, the sanitizers of the present invention correspond to a natural, non-corrosive, non-irritant product, contrarily to chlorine or other commercial sanitizers.

Currently, the food industry applies sanitary barriers to control *L. monocytogenes*. This means applying a rigorous control at every process points from raw materials to finished products, through the implementation of the HACCP system (Hazard Analysis in Critical Control Points). This is achieved by applying strict sanitizing programs using chemical products such as alcohol, chlorine dioxide, quaternary ammonium compounds, peracetic acid, sodium hypochlorite and the like. In general, the products used in the industry are described as irritant and/or having cumulative effects in humans, including carcinogenic effects, and so companies have to exert a permanent control of used dosages.

In the international state of the art, only 2 documents were found related to some extent to the present invention. The first of these documents is the U.S. Pat. No. 5,451,369, which is directed to the use of a bacteriocin (nisin) to be applied in aqueous form on surfaces, containers or substances that are in contact with food. This patent has a wide antimicrobial spectrum, contrarily to the sanitizer described in this invention, which has a specific inhibitory effect for the pathogen *L. monocytogenes*. On the other hand, the U.S. Pat. No. 6,054,163 describes a bacteriocin produced by the strain *Carnobacterium piscicola* JG126, a method to preserve food and the antimicrobial effect of the bacteriocin in food and beverages, including the pathogen *L. monocytogenes*. The surface sanitizer described in the present application differs from the abovementioned patents because it is based on fermentation products of selected LABs with demonstrated antagonistic capacity against *L. monocytogenes*. These LABs correspond to new and native strains isolated at the Austral university of Chile (UACh) and deposited at the ATCC. Finally, the surface sanitizers of the present invention differ in its application form, in the formulations presented hereinbelow and in the inhibitory effects against *L. monocytogenes*.

Currently, as it was mentioned several times before, chemical sanitizers are used in the industry, which have the disadvantage that a thorough cleaning must be performed in place prior to application and in some cases where *L. monocytogenes* is very well established on the surface the pathogen is not completely eliminated.

The surface sanitizer herein described is a biological product able to be brought to an industrial scale. It can be directly applied on food industry surfaces where *L. monocytogenes* is a real threat and a production limitation.

DETAILED DESCRIPTION OF THE INVENTION

Figure 1:
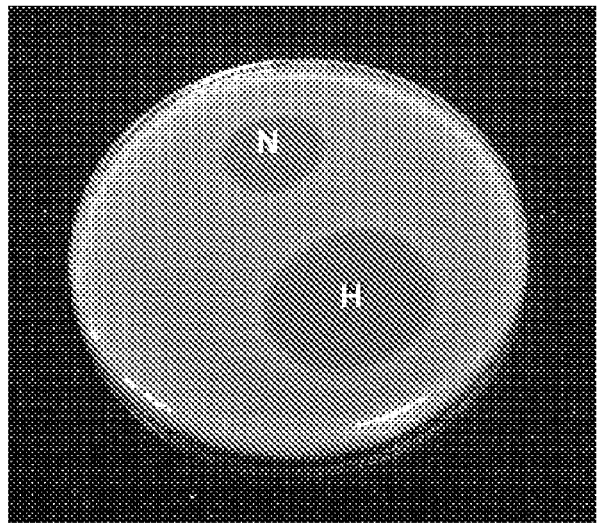
FIG. 1: Effect of the surface sanitizer (H) and Nisin alone (N) (1,000 IU/mL) on a lawn containing five *L. monocytogenes* strains.

The present invention discloses applications for three new native strains, two from the species *Carnobacterium maltaromaticum* ATCC® PTA-9380 and ATCC® PTA-9381 and the other from the species *Enterococcus mundtii* ATCC® PTA-9382, to obtain a formulation and surface sanitizers useful to control *L. monocytogenes*. The formulation of the invention, as well as the liquid and solid sanitizers, mainly comprises these three new LAB strains and nisin. The use of this sanitizer as biocontrol agent with antagonistic action against *L. monocytogenes*, the causal agent of listeriosis, a food-borne disease, is also disclosed. The 3 strains contained in the sanitizer have been tested and characterized as GRAS.

The formulations developed and described in the present invention to control *L. monocytogenes* have demonstrated their efficacy against different strains of this pathogen. Our results show that the liquid and solid sanitizers obtained from the formulation are able to eliminate *L. monocytogenes* from the biofilms formed in vivo on stainless steel, rubber and Teflon. These new sanitizers have been also compared to other currently available commercial sanitizers used in the food industry by means of in vitro applications on a lawn of *L. monocytogenes*, observing that the present invention is clearly more effective than the majority of the evaluated commercial products to reduce *L. monocytogenes* count.

The three new strains contained in the formulation of the invention were isolated at the Austral University of Chile. *C. maltaromaticum* ATCC® PTA-9380 and *E. mundtii* ATCC® PTA-9382 were isolated from cold-smoked vacuum packed salmon, and the strain *C. maltaromaticum* ATCC® PTA-9381 was isolated from samples of vacuum packed meat Currently, these 3 strains are freeze-dried and are also kept frozen at −80° C. as part of the strain collection of the Biological Products Laboratory of the Faculty of Agricultural Sciences of the Austral University of Chile. They show a tested and demonstrated antagonistic action against the pathogen *L. monocytogenes*. These new strains were identified as 2 *C. maltaromaticum* strains and 1 *E. mundtii* strain that were deposited at the ATCC® on Jul. 17, 2008 under access numbers ATCC®PTA-9380, ATCC® PTA-9381 and ATCC® PTA-9382, respectively. These bacterial strains constitute the biological base of the formulation and the surface sanitizers disclosed in the present invention.

The strains ATCC® PTA-9380, ATCC® PTA-9381 and ATCC® PTA-9382 were molecularly characterized using a 16S rDNA assay, the results of which are shown in Table 1. Furthermore, the same strains were described by performing the usual and widely known staining and biochemical assays used in microbiology. The results are shown in Table 2.

TABLE 1

Results of the molecular characterization of three strains antagonistic of *L. monocytogenes* isolated at the Austral University of Chile and registered at the ATCC ® using 16S rDNA assays.

| Strain | Identification |
|---|---|
| ATCC ® PTA-9380 | 90% similarity with *Carnobacterium maltaromaticum* |
| ATCC ® PTA-9381 | 97% similarity with *Carnobacterium maltaromaticum* |
| ATCC ® PTA-9382 | 98% similarity with *Enterococcus mundtii* |

Colonies of the strains ATCC® PTA-9380 and ATCC® PTA-9381 are white, small and have a creamy aspect on D-MRS agar (Schillinger, U. y Stiles, M. E. 1993. Bacteriocins production by *Carnobacterium piscicola* LV 61. Int. Journal Food Microbiology 20: 131-147), a medium comprising water, peptone proteose digest 10 g/L, meat extract 10 g/L, yeast extract 5 g/L, sucrose 20 g/L, Tween 80 1 g/L, ammonium citrate 2 g/L, magnesium sulfate 0.1 g/L and manganese sulfate 0.05 g/L, and dipotassium phosphate 2 g/L at a pH of 6.5±0.2; and on Soy Tripticase Agar (STA) (BECKTON, DICKINSON AND COMPANY) comprising: casein pancreatic digest 17 g/L, papain soy digest 3 g/L, dextrose 2.5 g/L, sodium chloride 5 g/L and dipotassium phosphate 2.5 g/L at a pH of 7.3±0.2. When plates are opened, a characteristic acid smell typical of fermented dairy products is perceived. Under the optical microscope, small Gram positive bacilli are observed with a size of around 0.5 ×2.0 μm, grouped in irregular arrangements.

Colonies of the strain ATCC® PTA-9382 are pale yellow, small and have a creamy aspect on MRS agar (Merck), a medium comprising: water, peptone proteose digest 10 g/L, meat extract 5 g/L, yeast extract 5 g/L, D(+)-glucose 20 g/L, Tween 80 1 g/L, ammonium citrate 2 g/L, sodium acetate 5 g/L, magnesium sulfate 0.1 g/L, manganese sulfate 0.05 g/L and agar 12 g/L, with a pH of 6.5±0.2; and on Soy Tripticase Agar (STA). Under the optical microscope, lanceolar Gram positive cocci are observed with a diameter of around 0.5×1.0 μm, in pairs or alone.

TABLE 2

Results of the staining, growth, biochemical and carbohydrate utilization assays of the two *C. maltaromaticum* strains and the *E. mundtii* strain deposited at the ATCC ® and the standard strains ATCC ® 43224 (*C. maltaromaticum*) y ATCC ® 43186 (*E. mundtii*).

| | Strain | | | | |
|---|---|---|---|---|---|
| Assay | *C. maltaromaticum* ATCC ® PTA-9380* | *C. maltaromaticum* ATCC ® PTA-9381** | *C. maltaromaticum* ATCC ® 43224 | *E. mundtii* ATCC ® PTA-9382*** | *E. mundtii* ATCC ® 43186 |
| Gram staining | G(+) Bacilli | G(+) Bacilli | G(+) Bacilli | G(+) Cocci | G(+) Cocci |
| Catalase assay | − | − | − | − | − |
| Growth at 15° C. | + | + | + | + | + |
| Arginine hydrolysis | + | + | + | + | + |
| Gas production from glucose | − | − | − | − | − |
| Fermentation of: | | | | | |
| Mannitol | + | + | + | + | + |
| Rhamnose | − | − | − | + | + |
| Mannose | + | + | + | + | + |
| Dulcitol | − | − | − | − | − |
| Xylose | − | − | − | + | + |

TABLE 2-continued

Results of the staining, growth, biochemical and carbohydrate utilization assays of the two
C. maltaromaticum strains and the E. mundtii strain deposited at the ATCC ® and
the standard strains ATCC ® 43224 (C. maltaromaticum) y ATCC ® 43186 (E. mundtii).

| | Strain | | | | |
| --- | --- | --- | --- | --- | --- |
| Assay | C. maltaromaticum ATCC ® PTA-9380* | C. maltaromaticum ATCC ® PTA-9381** | C. maltaromaticum ATCC ® 43224 | E. mundtii ATCC ® PTA-9382*** | E. mundtii ATCC ® 43186 |
| Inositol | − | − | − | − | − |
| Ribose | + | + | + | + | + |

Assays performed according to Schillinger and Lücke, 1987. Identification of lactobacilli from meat and meat products. Food Microbiology 4(3): 199-208.
*Strain ATCC ® PTA-9380 isolated from cold smoked vacuum packed salmon.
**Strain ATCC ® PTA-9381 isolated from vacuum packed meat.
***Strain ATCC ® PTA-9382 isolated from cold smoked vacuum packed salmon.

In the following section, the formulation of the surface sanitizers to be applied and used in the food industry or any other place where food is processed or manipulated is described.

Biological component of the inactivated fermentate (IF), main component of the formulation and the surface sanitizers.

The biological components of the present invention are LAB strains that were isolated from foods. The strain C. maltaromaticum ATCC® PTA-9380 was isolated from samples of cold-smoked vacuum packed salmon, the strain C. maltaromaticum ATCC® PTA-9381 was isolated from samples of vacuum packed meat, and the strain E. mundtii ATCC® PTA-9382 was isolated from samples of cold-smoked vacuum packed salmon. These procedures were carried out at the Austral University of Chile, in the city of Valdivia.

To manufacture an inactivated fermentate (IF) from the frozen strains ATCC® PTA 9380 y ATCC® PTA-9381, each one is inoculated in D-MRS broth and incubated at 25±2° C. for 24 to 48 h. Subsequently, both strains are separately inoculated at a 1% concentration in D-MRS broth and incubated for 24 to 48 h at 25±2° C. with shaking between 50-300 rpm. To obtain the IF of the frozen strain ATCC® PTA-9382, this strain is prepared as an inoculum in MRS broth and incubated at 30±2° C. for 24 to 48 h. Subsequently, the strain is separately inoculated at a 1% concentration in MRS broth and incubated for 24 to 48 h at 30±2° C. with shaking between 50-300 rpm.

The pH of the final culture of each strain is adjusted between 6.0-7.0 using a suitable base, such as NaOH, KOH, and the like, and subsequently subjected to an inactivating treatment, such as e.g. heat, sonication and the like, with the purpose of inactivating the cells. Inhibitory substances are not affected and remain active. Each treated culture corresponds to an Inactivated Fermentate that is preferably obtained by heat inactivation to provide a "Thermally Treated Fermentate" or TTF.

The heat treatment consists in subjecting the culture of the strains ATCC® PTA-9380 and ATCC® PTA-9381 to a temperature from 50 to 121° C., preferably 65° C., for a period from 5 to 20 minutes, preferably 10 minutes, with manual stirring every 3 to 10 minutes; the culture of the strain ATCC® PTA-9382 is subjected to a heat treatment at a temperature from 50 to 121° C., preferably at 70° C., for a period from 5 to 20 minutes, preferably 10 minutes, with manual stirring every 3 to 10 minutes.

The inactivation of lactic strains is assessed by inoculating 100 µl of each IF on separate D-MRS agar and MRS agar plates (Merck). Plates are incubated for 48 h at 30° C. As no colony growth is observed in any agar plate, inactivation of the LAB strains is assessed.

The strains ATCC® PTA-9380, ATCC® PTA-9381 and ATCC® PTA-9382 were molecularly characterized using a 16S rDNA assay, the results of which are shown in Table 1; the strains were also described through Gram staining and several well known biochemical assays usually used in microbiology, results are shown in Table 2.

ATCC® PTA-9380 and ATCC® PTA-9381 colonies are white, small and have a creamy aspect, and were cultured on D-MRS agar and Soy Tripticase Agar. When plates containing these strains growing in the abovementioned media are opened, an acid smell can be perceived, which is characteristic of a fermented dairy product. Under the optical microscope, small Gram positive bacilli are observed with a size of around 0.5×2.0 µm, grouped in irregular arrangements.

The strain ATCC® PTA-9382 was molecularly characterized using a 16S r DNA assay, the results of which are shown in Table 2; this strain was also described through Gram staining and several well known biochemical assays usually used in microbiology, which results are shown in Table 2.

Colonies of the strain ATCC® PTA-9382 are pale yellow, small and have a creamy aspect, and were cultured on MRS agar and Soy Tripticase Agar. Under the optical microscope, lanceolar Gram positive cocci are observed with a diameter of around 0.5×1.0 µm, in pairs or alone.

For the preparation of nisin, this is diluted in HCl 0.02 N, which provides a concentration ranging from 5,000 to 50,000 IU/mL at a pH close to 2.0. pH is adjusted at 3.0 with NaOH 0.5 N. This solution is filter-sterilized using suitable filters, such as e.g. 0.22 µm filters. From this solution, necessary amounts are taken to achieve a final concentration ranging from 500 to 5,000 IU/mL, preferably 1,000 IU/mL.

The final mixture of the 4 active ingredients forms the sanitizing formulation of the present invention. As described herein, the sanitizing formulation comprises between $10^7$-$10^9$ CFU/mL independently of each of the strains ATCC® PTA-9380, ATCC® PTA-9381 and ATCC® PTA-9382 and from 500 to 5,000 IU/mL of nisin.

In general, when Colony Forming Units are mentioned or reference is made to them in relation to inactivated cultures, it must be understood that this determination is made prior to the inactivation of the respective culture.

This sanitizing formulation can be embodied in different presentations of sanitizing products; two preferred sanitizing product forms are liquid and encapsulated solid.

The liquid surface sanitizer is obtained from an equal parts mixture of the IF of each LAB strain plus nisin at a final concentration ranging from 500 to 5,000 IU/mL. Given the manufacture procedure, the final concentration of each LAB is between $10^7$-$10^9$ CFU/mL. To achieve the final desired concentration, the formulation is optionally diluted with water in a ratio from 1:1 to 1:15 to provide the liquid surface sanitizer. The liquid sanitizer form is used to control *L. monocytogenes* on working surfaces and devices in the food industry. The product maintains the antagonistic characteristics for 3 months when stored at refrigerator temperature (6±2° C.). For manipulating the product, no protection is necessary. The product is used undiluted, applied by spraying. Contact time is from 10 to 30 minutes, preferably 15 minutes. The product can be applied on working surfaces, equipment or devices.

The solid surface sanitizer can comprise different embodiments, always maintaining the abovementioned active principles. In a preferred embodiment, the solid sanitizer can be processed to provide capsules. In another preferred embodiment, the solid sanitizer can be deposited on a mesh-type fabric.

The encapsulated solid surface sanitizer is obtained from equal portions of the IF of the three LAB strains as previously described, plus nisin at a final concentration ranging from 500 to 5,000 IU/mL and a concentration of each LAB strain ranging from $10^7$-$10^9$ CFU/mL biotrapped in an alginate matrix. Sodium alginate is used at a concentration ranging from 1 to 5% w/v and maltodextrin is used at a concentration ranging from 5 to 10% w/v.

To prepare a preferred embodiment of the encapsulated solid sanitizer, the following steps must be pursued:

a. Firstly, an homogenate for IF encapsulation is prepared using a sodium alginate solution at a concentration ranging from 1 to 5% and maltodextrin at a concentration ranging from 5 to 10%. Powdered maltodextrin and alginate are mixed in a suitable container, 300 to 500 mL of distilled water are added and the mixture is homogenized until viscous, generally for 5 to 30 min.
b. The mixture from the previous step is subjected to sterilization by autoclaving, e.g. at 100° C. for 5 min.
c. The sterile mixture is cooled with constant stirring from 50 to 300 rpm until reaching 25° C.
d. IFs from the three LAB strains are added in equal amounts (1:1:1) plus a suitable volume of nisin (at an initial concentration of 10,000 IU/mL), in such a way as to achieve a final nisin concentration ranging from 500 to 5,000 IU/mL.
e. The final mixture is passed through a suitable encapsulating equipment configured to produce capsules from 3 to 8 mm in diameter, preferably 5.6 mm. To coagulate the gel and form capsules, these must be kept in contact with $CaCl_2$ (0.1 M) from 5 to 15 min., and then partially dehydrate with forced air at 25±0.2° C. until reaching a water activity $A_w$ around 0.86-0.89, preferably Aw 0.88, for 15 to 45 min, after which the capsules reach a final diameter of 2.5±0.2 mm for their use.

One gram of encapsulated solid sanitizer comprises about 86 capsules. These capsules are used to control *L. monocytogenes* on surfaces, gutters and floors in the food industry. The duration (stability) of the capsules is around 1 year when stored refrigerated or at room temperature, or even in a range as high as 25° C. to 40° C. For manipulating the product, no protection is necessary. To dose the product, the recommendation is applying 1 g of capsules to a 50 to 90 $cm^2$ surface, changing the capsules every 8 to 24 h.

In another preferred embodiment, the solid sanitizer can be formed as a mesh-type cover.

The solid surface sanitizer is made by coating a mesh-type fabric, which constitutes a support. The product is obtained from an equal parts mixture of the IF of the three LAB strains plus nisin at a final concentration ranging from 500 to 5,000 IU/mL and a concentration of each LAB strain ranging from $10^7$-$10^9$ UFC/mL, biotrapped in an alginate and maltodextrin matrix. Sodium alginate is used at a concentration ranging from 1 to 5% w/v and maltodextrin is used at a concentration ranging from 5 to 10% w/v.

To prepare the mesh sanitizer, the following steps must be pursued:

a. Firstly, an homogenate for IF biotrapping is prepared using a sodium alginate solution at a concentration ranging from 1 to 5% and maltodextrin at a concentration ranging from 5 to 10%. Powdered maltodextrin and alginate are mixed in a suitable container, 300 to 500 mL of distilled water are added and the mixture is homogenized until viscous, generally for 5 to 30 min.
b. The mixture from the previous step is subjected to sterilization by autoclaving, e.g. at 100° C. for 5 min.
c. The sterile mixture is cooled with constant stirring from 50 to 300 rpm until reaching 25° C.
d. IFs from the three LAB strains are added in equal amounts (1:1:1) plus a suitable volume of nisin (at an initial concentration of 10,000 IU/mL), in such a way as to achieve a final nisin concentration ranging from 500 to 5,000 IU/mL.
e. The mixture is coagulated by deposit in a sterile tray-type container and a suitably sized mesh for gutters or drainages, e.g. 70 cm long and 15 cm wide, is introduced into the container. The mesh support is a synthetic fabric similar to a net or sterile gauze. The mesh pieces are completely covered with a layer of mixture and subsequently removed to eliminate the excess, and then are placed into a container with a 0.1 M calcium chloride solution, a coagulant substance that causes the mixture to coagulate over the mesh (FIG. 4). The contact time with $CaCl_2$ ranges from 5 to 15 min., then meshes are removed and partially dehydrated at 25±0.2° C. in an incubation chamber with forced air convection until reaching a water activity $A_w$ around 0.72 to 0.80, preferably 0.75, for 1 to 3 h.
f. After 2 h at 25° C., a 0.75 water activity is obtained.

These meshes are used to control *L. monocytogenes* on gutters in the food industry. For manipulating the product, no protection is necessary.

The surface sanitizer of this invention has two surprising effects in comparison with the traditional application of nisin: first, it shows better inhibition of *L. monocytogenes* as can be seen in FIG. 1 and, second, it has a sustained effect in time, contrarily to nisin alone, as demonstrated in vivo and in foods by Schillinger, U., Becker, B., Vignolo, G. and Holzapfel, W. H. (2001). *L. monocytogenes* developed resistance and grew again after 48 h of incubation in a culture broth containing only nisin, but this regrowth of *L. monocytogenes* is avoided using the formulation of this invention comprising nisin plus a mixture of LAB strains. In a food like tofu, stored at 10° C., the formulation of the invention comprising a combination of nisin and LAB strains was also effective, inhibiting the development of *L. monocytogenes* to undetectable levels. By contrast, in the presence of nisin alone, *Listeria* started to grow again from the second day onward (Schillinger, U., Becker, B., Vignolo, G. and Holzapfel, W. H. 2001, "Efficacy of nisin in combination with protective cultures against *Listeria monocytogenes* Scott A in Tofu". International Journal of Food Microbiology 71:159-168). In FIG. 1, inhibition halos are shown in a bacterial lawn of a mixture of five *L. monocytogenes* strains against nisin alone (N) and to the liquid surface sanitizer of the invention (H).

The antagonistic activity of the three LAB strains ATCC® PTA-9380, ATCC® PTA-9381 y ATCC® PTA-9382 was assessed at two temperatures, 25° C. and 10° C., in a pH ranging from 4.5 to 9.0 and in the presence of two NaCl concentrations, 1.5% and 3.0%, in the growth medium. The results indicated for the LAB strains ATCC® PTA-9380 and ATCC® PTA-9381 that more antagonistic activity was measured in the broth when growth was performed at 10° C. instead of 25° C. and with a broth pH adjusted at 6.5, 7.0, 8.0, 8.5 or 9.0. By contrast, for strain ATCC® PTA-9382 higher antagonistic activity was observed when growth was performed at 25° C. with a broth pH adjusted at 6.5, 7.0 or 7.5. NaCl concentrations of 1.5% and 3.0% in the culture broth did not notably affect the antagonistic activity of the three LAB strains incubated at 25° C. At 10° C., antagonistic activity was lower at both NaCl concentrations. The strain that was most affected by the presence of NaCl at 10° C. was ATCC® PTA-9382. Antagonistic stability of the IF was determined during 21 storage days at different temperatures from −20° C. to 25° C., the stability at 4° C. at a pH ranging from 4.5 to 6.5 during 21 days and the stability after heat treatments at 63° C./30 min, 100° C./30 min, 121° C./10 min and 121° C./15 min were also assessed. The results indicated that the antagonistic activity of the IF was similar and hence stable at each storage temperature during 21 days. The antagonistic activity of the IF was also not affected during storage at 4° C. at different pH values. During heat treatments, loss of activity was only observed at 121° C. for 15 min and, by contrast, at 121° C. during 10 min the antagonistic activity was conserved.

The innocuousness of the LAB strains ATCC® PTA-9380, ATCC® PTA-9381 and ATCC® PTA-9382 and their antagonistic products (IF) were assessed by inoculating rats with the crude extract of the formulation of the invention and no deaths or adverse effects on organs by histopathological tests were observed.

The liquid and encapsulated solid sanitizers have the following benefits and advantages:

Both formulations are useful to prevent and control *L. monocytogenes* and have proven efficacy against biofilms formed by different *L. monocytogenes* strains, specifically in food processing lines (transport, processing and storage). The use of these sanitizers can be extended to any other food industry because they show high safety standards and applicability in food industries such as meat, salmon, dairy and vegetable industries, since *L. monocytogenes* is a pathogenic agent that causes severe human health problems and is present in a large majority of places where food is processed. Furthermore, the sanitizer of the invention can be applied and used during food processing with no need to stop the process. These products are compatible with an organic label, since they are biologically-derived. They are easy to apply. These products are 100% biodegradable. They can be applied with people in place. These products are no toxic for humans or animals and are not corrosive, volatile, metallic, irritant, oxidizable or inflammable.

APPLICATION EXAMPLES

Example 1

Preparation of Inactivated Fermentate (IF) by Heat Treatment to Produce a Thermally Treated Fermentate (TTF)

Biological component of the TTF, main component of the surface sanitizer: isolation, characterization and demonstration of the antagonistic activity against *L. monocytogenes*.

To obtain the desired active substance of the sanitizers (TTFs), a fermentate must be produced by growing the three lactic species in D-MRS and MRS broth, respectively. For the strains ATCC® PTA-9380 and ATCC® PTA-9381, D-MRS broth was used with incubation at 25° C. for 24 h, and for the strain ATCC® PTA-9382, MRS broth was used with incubation at 30° C. for 24 h. The incubation was performed in an orbital shaker (150 rpm) (BARNSTEAD INTERNATIONAL, MODEL 4000-ICE) until reaching counts of $10^7$-$10^9$ CFU/mL. pH was adjusted to 6.5 in the final fermentation product with NaOH 0.1 N and the product was subsequently subjected to a heat treatment (TTF) to inactivate the cells, which was performed in a thermoregulated Memmert bath. Strains ATTC® PTA-9380 and ATTC® PTA-9381 were subjected to a temperature of 65° C. for 10 min with manual stirring every 5 min, while strain ATTC® PTA-9382 was subjected to a temperature of 70° C. for 10 min with manual stirring every 5 min.

When said thermal treatment was performed, inhibitory substances were not affected and remained active (Table 3), since in the TTFs the inhibitory activity only varied for strain ATTC® PTA-9382.

TABLE 3

Results expressed in activity units (AU) of the fermentates before and after the heat treatment (TTF) of the standard strains *C. maltaromaticum* ATCC ® 43224 and *E. mundtii* ATCC ® 43186, and strains *C. maltaromaticum* ATCC ® PTA-9380, ATCC ® PTA-9381 and *E. mundtii* ATCC ® PTA-9382, against a bacterial lawn comprising a mixture of five strains of *L. monocytogenes*.

|  | Activity units (AU/mL) Before heat treatment | Activity units (AU/mL) After heat treatment |
|---|---|---|
| *C. maltaromaticum* ATCC ® 43224 | 100 | Undetectable |
| *C. maltaromaticum* ATCC ® PTA-9380 | 3,200 | 3,200 |
| *C. maltaromaticum* ATCC ® PTA-9381 | 3,200 | 3,200 |
| *E. mundtii* ATCC ® 43186 | Undetectable | Undetectable |
| *E. mundtii* ATCC ® PTA-9382 | 1,638,400 | 819,200 |

Inactivation of the lactic strains was assessed by inoculating 100 µl of TTF on separate D-MRS agar plates and 100 µl of TTF on a MRS agar plate (Merck). No colony growth was observed after 48 h of incubation at 30° C. in any of the D-MRS or MRS agar plates.

Example 2

Preparation of the Formulation to Control *Listeria monocytogenes*

The LAB TTFs from Example 1 were mixed in equal proportions (1:1:1). In this case, 300 mL of each TTF were mixed to prepare 1 L of final liquid formulation. To this mixture, 100 mL of nisin were added (10,000 IU/mL).

Hence, a final formulation was obtained comprising nisin at a concentration of 1,000 IU/mL (v/v).

To prepare nisin (10,000 IU/mL), 1000 mg of Nisaplin® ($10^6$ IU, Danisco) were diluted in 100 mL of HCl 0.02 N, providing a concentration of 10,000 IU/mL at a pH around 2.0. pH was adjusted at 3.0 with NaOH 0.5 N. This solution was sterilized by filtration (0.22 µm filter, Millipore, USA).

Example 3

Preparation of the Liquid Sanitizer

To prepare 1 L of liquid sanitizer, 500 mL of the formulation of Example 2 were diluted with water to 1 L of liquid sanitizer. Hence, a concentration of 500 IU/mL (v/v) of nisin is provided in the liter of liquid sanitizer. The final liquid is the liquid sanitizer of the invention.

Example 4

Preparation of the Encapsulated Sanitizer

Preparation of the homogenate. Firstly, an homogenate for TTF encapsulation is prepared using a sodium alginate solution (Gely Gum 7228, Gelymar) at a concentration of 2% and maltodextrin (Prinal) at a concentration of 8%. In a glass beaker, maltodextrin and powdered alginate were mixed and 480 mL of distilled water were added, then the mixture was homogenized until viscosity developed after 15 min and autoclaved at 100° C. for 5 min. The sterile sample was cooled in a shaker (VELP Scientifica) down to 25° C. and TTFs from the three LAB strains were added in equal proportions (1:1:1), i.e. 200 mL of each TTF plus 120 mL of nisin (initially at 10,000 IU/mL v/v) and 480 mL of the sterile alginate-maltodextrin mixture were added for a total volume of 1,200 mL. This mixture passed through an encapsulator (NISCO) with a 400 μm nozzle and capsules with 5.6 mm in diameter were obtained, which were partially dehydrated with forced convection air at 25±0.2° C. for 30 min until reaching a water activity $A_w$ of 0.88 and a final capsule diameter of 2.5±0.2 mm.

Example 5

Determination of Units of Antagonistic Activity Against L. monocytogenes

Determination of the activity units (AU) of the TTFs of the standard strains C. maltaromaticum ATCC® 43224 and E. mundtii ATCC® 43186, and strains C. maltaromaticum ATCC® PTA-9380, ATCC® PTA-9381 and E. mundtii ATCC® PTA-9382, in vitro against a bacterial lawn comprising a mixture of five strains of L. monocytogenes.

The antagonistic activities (activity units per mL, AU/mL) of the strains ATCC® PTA-9380, ATCC® PTA-9381 and E. mundtii ATCC® PTA-9382 were compared with those of the standard strains C. maltaromaticum ATCC® 43224 and E. mundtii ATCC® 43186. The drop-on-lawn method was used, wherein a Petri dish with 15 mL of soy trypticase agar (STA) is covered with a 18 h-bacterial culture lawn ($10^5$ CFU/mL final concentration) of a mixture of five strains of L. monocytogenes. To get the bacterial lawn, 7 mL of semi-solid STA (0.75% agar) were inoculated with 0.7 mL (700 μL) of a culture diluted 100-fold in 0.05 M phosphate buffer pH 7.0 ($NaH_2PO_4+Na_2HPO_4$). 20 μL of seriated dilutions of the TTFs were put on the bacterial lawn.

To obtain test TTFs, a formulation of liquid sanitizer was prepared as described in Example 1. For comparison, a liquid TTF was similarly obtained from a preparation of the known standard strains ATCC® 43186 and ATCC® 43224.

pH of the bacterial cultures was adjusted to 6.5 using 0.1 N NaOH and the cultures were subjected to a heat treatment in a thermoregulated bath (Memmert) at 65° C. for 10 min for the strains ATCC® PTA-9380, ATCC® PTA-9381 and ATCC® 43224, and at 70° C. for 10 min for the strains ATCC® 43186 and ATCC® PTA-9382.

The plates with seriated dilutions of the TTFs were incubated for 48 h at 4° C., subsequently at 25° C. for 12 h, and after this last incubation period inhibition halos were measured.

To evaluate the result, formation of inhibition halos around the inoculation zone of the TTF dilutions was observed. To calculate the activity units per mL (AU/mL) for each TTF, a positive is defined as the largest dilution for which an inhibition halo is observed, and activity units are the reciprocal of said dilution expressed as per mL.

The results of activity unit measurements are shown in Table 4.

The five L. monocytogenes strains used in the antagonism test are two standard strains (ATCC® 19115 isolated from humans and ATCC® 15313 from rabbit) and three strains from the strain collection of the Biological Products Laboratory of the Faculty of Agricultural Sciences of the Austral University of Chile, isolated from cold smoked salmon (strains Lsa 1/00, Lsa 3/00 and Lsa 4/00). These strains are freeze-dried and are also kept frozen at −80° C.

The possibility of combining the three TTF plus nisin in the organic sanitizer described in the present invention allows the four active components to act together against L. monocytogenes and, in case that L. monocytogenes develops resistance against one of these components, the others continue their action.

TABLE 4

Results of activity units (AU) of the TTFs of the standard strains C. maltaromaticum ATCC ® 43224 and E. mundtii ATCC ® 43186, and strains C. maltaromaticum ATCC ® PTA-9380, ATCC ® PTA-9381 and E. mundtii ATCC ® PTA-9382, against a mixture of five strains of L. monocytogenes.

|  | Activity units (AU/mL) |
| --- | --- |
| C. maltaromaticum ATCC ® 43224 | Undetectable |
| C. maltaromaticum ATCC ® PTA-9380 | 3,200 |
| C. maltaromaticum ATCC ® PTA-9381 | 3,200 |
| E. mundtii ATCC ® 43186 | Undetectable |
| E. mundtii ATCC ® PTA-9382 | 819,200 |

Example 6

Maximal Inhibitory Dilution of the Liquid Sanitizer Against a Mixture of Five of L. monocytogenes Strains The assay was carried out using the liquid sanitizer containing the TTFs of the strains ATCC® PTA-9380, ATCC® PTA-9381 and ATCC® PTA-9382, plus nisin (1,000 IU/mL) against a mixture of five L. monocytogenes strains ($10^6$ CFU/mL) in low-nutrient ST broth (10 g per liter). Each L. monocytogenes strain is cultured separately in ST broth for 18 h at 25° C. to achieve a concentration of $10^9$ CFU/mL. The five L. monocytogenes strains were mixed and diluted to a final concentration of $10^6$ UFC/mL in low-nutrient ST broth.

The undiluted sanitizer has an initial activity of $8.2\times10^5$ AU/mL. This sanitizer is added to low-nutrient ST broth containing a mixture of Listeria ($10^5$ CFU/mL) in seriated dilutions: half (1×) ($4.1\times10^5$ AU/mL), 15 times (15×) ($5.1\times10^4$ AU/mL), 50 times (50×) ($1.6\times10^4$ AU/mL), 100 times (100×) ($8.2\times10^3$ AU/mL), 200 times (200×) ($4.1\times10^3$ AU/mL), 500 times (500×) ($1.6\times10^3$ AU/mL) and 2000 times (2000×) ($4.0\times10^2$ AU/mL).

Each sanitizer was left to act at 10° C. for 15 and 30 minutes in the respective tube. The mixture of five *L. monocytogenes* strains ($10^6$ CFU/mL) was used as a control without sanitizer. After the respective period of action, a plate counting was carried out on ST agar incubated at 30° C. for 24 h.

Figure 2:
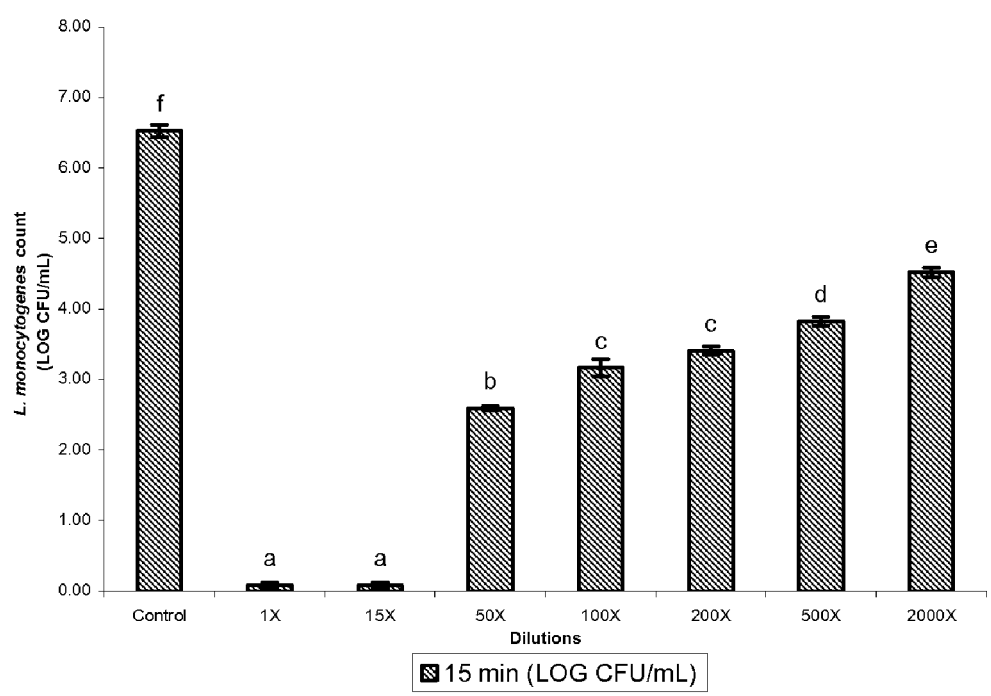
FIG. 2: Maximal inhibitory dilution of the surface sanitizer to destroy a mixture of five *L. monocytogenes* strains in ST broth at 10° C. Small letters indicate significant differences with $p<0.05$.

In FIG. 2, *L. monocytogenes* counts obtained when applying the different sanitizer dilutions are shown. The statistical analysis indicates that significant ($p<0.05$) reductions were observed in bacterial counts in comparison with the initial count for all the assayed concentrations. The surface sanitizer can be diluted 15 times and is still effective to reduce 6 logarithmic cycles of *L. monocytogenes* with an initial population of $10^6$ CFU/mL.

Example 7

In Vitro Inhibition Capacity of the Encapsulated Surface Sanitizer Against a Bacterial Lawn of a Mixture of Five *L. monocytogenes* Strains The object of this assay was to determine the diffusion of the encapsulated surface sanitizer with time and its antagonistic effect against a mixture of five *L. monocytogenes* strains. For this assay, capsules of the surface sanitizer were prepared using a mixture of equal proportions of the three TTFs of the lactic strains ATCC® PTA-9380, ATCC® PTA-9381 and ATCC® PTA-9382, plus nisin (1,000 UI/mL) biotrapped in an alginate-maltodextrin matrix. The capsules for different diffusion times were placed in ST agar plates and incubated at 10° C. to allow diffusion for the specified times up to five days. For time zero, the capsules are left in contact with the agar only for 10 min. When the allowed diffusion time is reached, the capsules are removed from the ST agar plates and covered with a bacterial lawn containing a mixture of the five *L. monocytogenes* strains ($10^5$ CFU/mL final concentration). Plates are subsequently incubated at 4° C. for 48 h and then at 25° C. for 14 h, with the purpose of visualizing the formation of inhibition halos produced by diffusion of the surface sanitizer that prevents the development of *L. monocytogenes* in the lawn. These halos are measured with a digital vernier caliper (Mitutoyo model CD-6"C).

Figure 3:
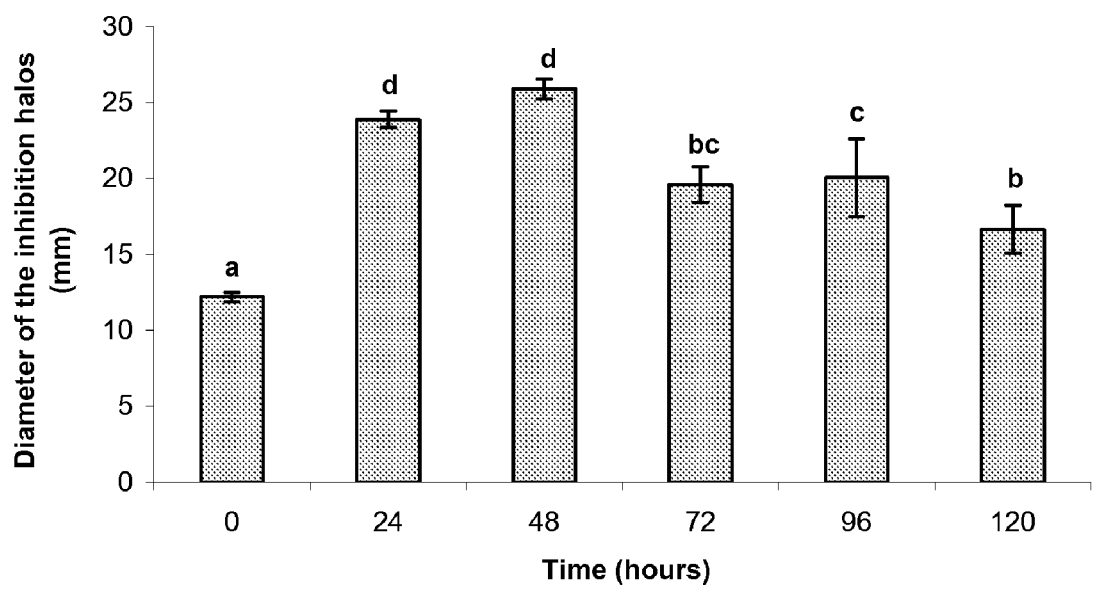
FIG. 3: Inhibition of a sample of five *L. monocytogenes* strains in a lawn with different diffusion times of an encapsulated sanitizer. Diffusion at 10° C. Small letters indicate significant differences with $p<0.05$.
Figure 4:
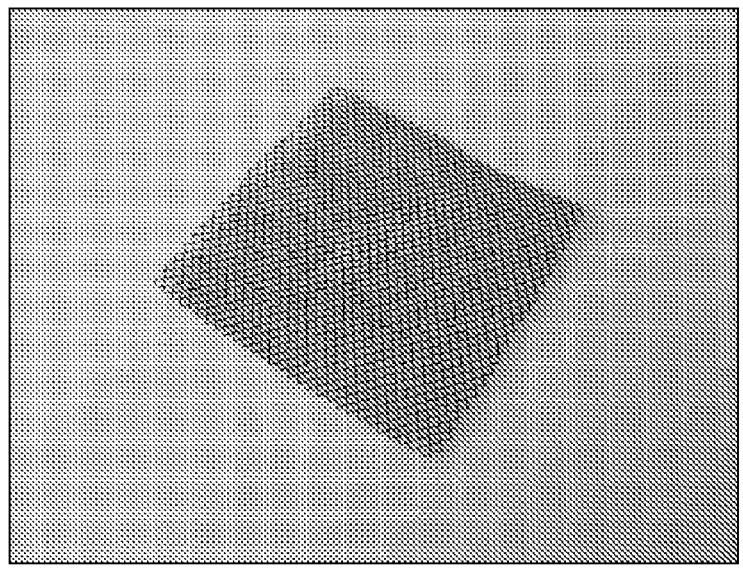
FIG. 4: Image of a mesh built using a 9×9 cm$^2$ fabric support together with the homogenized mixture, IF and nisin.

FIG. 3 shows the diameters of the halos formed by the encapsulated surface sanitizer after different diffusion times. After a contact of 10 min with the agar (time zero) there is already some diffusion of the sanitizer to the surface, which can be assessed by the presence of inhibition halos. As contact time elapses, diffusion from the capsules increases with a maximum at 24 and 48 h ($p<0.05$). This is favorable since capsules are to be used in places wherein they will stay for several hours (gutters, drainages) and a constant diffusion in time is needed in these circumstances. Even after five days there is still diffusion of the surface sanitizer from the capsules.

Example 8

In Vitro Antagonism Assays of the Mesh

Figure 5:
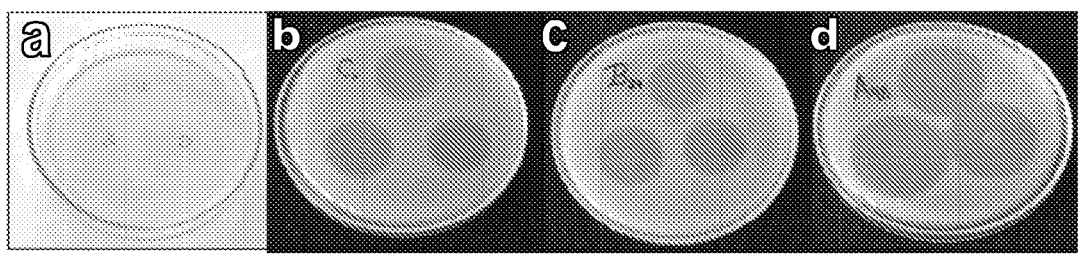
FIG. 5: Inhibition halos with different diffusion times of the biocontroller of the mesh: a) Disposition mode of the mesh pieces on an ST agar plate; b) Inhibition halos at T0 (10 min of diffusion); c) Inhibition halos at T24 (24 h of diffusion at 10° C.); d) Inhibition halos at T48 (48 h of diffusion at 10° C.).

Equally-sized pieces of the mesh with the biocontroller are placed on a bacterial lawn with a mixture of five *L. monocytogenes* strains and the sanitizer is allowed to diffuse for 10 min, 24 h, 72 h, 96 h and 120 h. At the end of each period, the mesh pieces are removed and the plate is covered with the mixture of *L. monocytogenes* strains. The plates are incubated and the presence of inhibition halos is observed. Inhibition halos are shown in FIG. 5, which increased with diffusion times, indicating a controlled and sustained release of the sanitizer in time.

Figure 6:
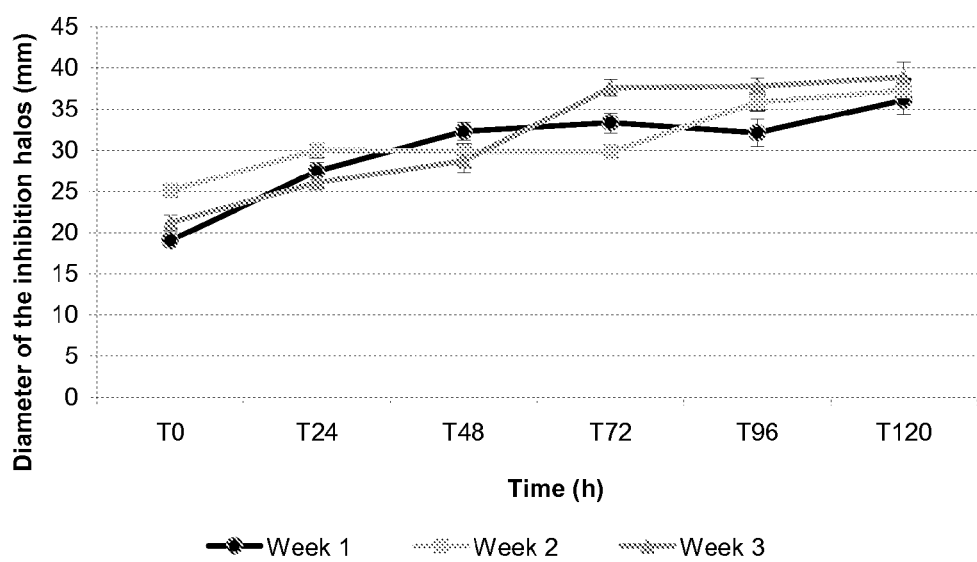
FIG. 6: Antagonistic activity of the meshes stored for 21 days at 4° C. on a lawn of *L. monocytogenes*.

The antagonistic activity of the mesh stored at 4° C. was also assayed. The mesh was stored for 3 weeks and in vitro activity assays were performed every 24 h. In FIG. 6 and Table 1 it is possible to observe that there were differences between the different meshes, but no activity losses were detected, since the mesh presented even less activity on the first week in comparison with the other two times. This can be due to the fact that the meshes had different thicknesses when prepared. It is also possible to observe an increase in the halo sizes with diffusion time (from 0 to 120 h) (FIG. 6).

TABLE 5

In vitro antagonistic action of TTFs on a bacterial lawn of five *L. monocytogenes* strains during three weeks of storage of the mesh at 4° C. Diameters of inhibition halos in mm. The values are averages of three observations of three replicates for each experiment.

| Time (h) | Week 1 | Week 2 | Week 3 |
| --- | --- | --- | --- |
| T0 | 19.03 ± 0.49 Aa | 25.12 ± 0.71 Ba | 21.23 ± 0.97 Aa |
| T24 | 27.47 ± 1.08 ABb | 30.04 ± 0.78 Bb | 26.07 ± 0.81 Ab |
| T48 | 32.32 ± 1.09 Ac | 29.87 ± 0.84 Bb | 28.75 ± 1.46 Bc |
| T72 | 33.36 ± 1.22 Acd | 29.81 ± 0.65 Bb | 37.63 ± 1.01 Cd |
| T96 | 32.14 ± 1.69 Ac | 35.88 ± 0.93 Bc | 37.80 ± 0.95 Bd |
| T120 | 36.15 ± 1.70 Ad | 37.33 ± 1.29 ABd | 38.90 ± 1.86 Bd |

*Capital letters indicate differences between different storage weeks for each incubation time.
**Small letters indicate differences between different incubation times for each storage week.

Deposit of Material

The following materials have been deposited with the American Type Culture Collection, 1801 University Blvd., Manassas, Va. 20110-2209, USA (ATCC):

| Material | ATCC Dep. No. | Deposit Date |
| --- | --- | --- |
| UACH-1 | PTA-9380 | 17 Jul. 2008 |
| UACH-2 | PTA-9381 | 17 Jul. 2008 |
| UACH-3 | PTA-9382 | 17 Jul. 2008 |

The invention claimed is:

1. A formulation useful to control *Listeria monocytogenes* wherein said formulation comprises:
   a fermentate formed by inactivated cultures of the strains *Carnobacterium maltaromaticum* ATCC ® PTA-9380, *Carnobacterium maltaromaticum* ATCC ® PTA-9381 and *Enterococcus mundtii* ATCC ® PTA-9382; and
   a bacteriocin nisin.

2. A formulation according to claim 1, wherein the culture medium of the inactivated cultures of the strains *C. maltaromaticum* ATCC® PTA-9380 and *C. maltaromaticum* ATCC® PTA-9381 is D-MRS and the culture medium of the inactivated cultures of the strain *E. mundtii* ATCC® PTA-9382 is MRS.

3. A formulation according to claim 1, wherein said formulation comprises a cell concentration of the strains *C. maltaromaticum* ATCC® PTA-9380, *C. maltaromaticum* ATCC® PTA-9381 and *E. mundtii* ATCC® PTA-9382 of $10^7$-$10^9$ CFU/mL, each independently, and nisin at a concentration ranging from 500 to 5,000 IU/mL.

4. A liquid surface sanitizer for the control of *L. monocytogenes* wherein said liquid surface sanitizer comprises the formulation of claim 1 optionally diluted with water in a ratio from 1:1 to 1:15.

5. A solid surface sanitizer for the control of *L. monocytogenes* wherein said solid surface sanitizer comprises the formulation of claim 1, sodium alginate at a concentration ranging from 1 to 5% w/v and maltodextrin at a concentration ranging from 5 to 12% w/v.

6. A method to obtain the formulation of claim 1, wherein said method comprises the steps of:
   obtaining fermentates from cultures of the strains *C. maltaromaticum* ATCC® PTA-9380, *C. maltaromaticum* ATCC® PTA-9381 and *E. mundtii* ATCC® PTA-9382 and subsequently inactivating said fermentates;
   mixing the inactivated fermentates of step (a) in equal proportions;
   adding a solution of nisin in such a way as to get a final nisin concentration ranging from 500 to 5,000 IU/mL.

7. A method to obtain the formulation according to claim 6, wherein in step (a) the cultures are inactivated through a heat treatment by subjecting the cultures to a temperature ranging from 50 to 121° C. for a period ranging from 5 to 20 minutes.

8. A method for preparing a liquid surface sanitizer according to claim 4, wherein said method comprises the step of diluting the formulation with water in a proportion ranging from 1:5 and 1:15 when the surface sanitizer is diluted.

9. A method for preparing a solid surface sanitizer comprising a formulation including a fermentate formed by inactivated cultures of the strains *Carnobacterium maltaromaticum* ATCC ® PTA-9380, *Carnobacterium maltaromaticum* ATCC ® PTA-9381, *Enterococcus mundtii* ATCC ® PTA-9382, a bacteriocin nisin, sodium alginate at a concentration ranging from 1 to 5% w/v, and maltodextrin at a concentration ranging from 5 to 12% w/v. wherein said method comprises:
   preparing a solution of sodium alginate at a concentration ranging from 1 to 5% w/v and maltodextrin at a concentration ranging from 5 to 10% w/v with distilled water and homogenizing the resulting mixture until viscosity develops for 5 to 30 minutes;
   Subjecting the mixture from the previous step to sterilization by autoclaving;
   cooling the sterile mixture with constant stirring from 50 to 300 rpm until reaching 25° C.;
   adding the formulation of claim 1 that comprises TTFs from the three LAB strains in equal amounts (1:1:1) and nisin in such a way as to achieve a final nisin concentration ranging from 500 to 5,000 IU/mL;
   coagulating the fmal mixture.

10. A method for preparing a solid surface sanitizer according to claim 9, wherein in step (e) the final mixture is coagulated either by passing the mixture through a suitable encapsulator equipment configured to produce capsules with a diameter ranging from 3 to 8 mm, which are partially dehydrated to get a water activity $A_w$ ranging from 0.86 to 0.89; or by putting the mixture in a sterile tray-type container and introducing into the mixture a supporting synthetic fabric mesh similar to a net or a sterile gauze, wherein mesh pieces are completely covered with a layer of the mixture, then said mesh pieces are removed, the excess mixture is eliminated and said mesh pieces are put into a container with a 0.1 M calcium chloride solution, and finally said mesh pieces are removed from the container and partially dehydrated at 25±0.2° C. to achieve a water activity $A_w$ ranging from 0.72 to 0.80.

11. A method for inhibiting or preventing growth of *L. monocytogenes* on surfaces where food is processed or manufactured, comprising applying the liquid surface sanitizer of claim 4 to the surface or device.

12. The method of claim 11, wherein said liquid sanitizer is applied by spraying onto the surfaces or device.

13. A method for inhibiting or preventing growth of *Listeria monocytogenes* in surfaces, gutters, floors and drainages, comprising applying the solid surface sanitizer of claim 5 to the surfaces, gutters, floors.

14. The method of claim 13, wherein said solid sanitizer is applied on gutters, floors, drainages and surfaces and replaced with fresh solid sanitizer every 8 to 24 hours.

15. An isolated bacterial strain belonging to genus *Carnobacterium* and species *maltaromaticum*, deposited on Jul. 17, 2008 under the accession number ATCC ® PTA-9380, wherein said strain are Gram-positive, bacillary bacteria, and exhibit antagonist activity against *Listeria monocytogenes*.

16. An isolated bacterial strain belonging to genus *Carnobacterium* and species *maltaromaticum*, deposited on Jul. 17, 2008 under the accession number ATCC ® PTA-9381, wherein said strain are Gram-positive, bacillary bacteria, and exhibit antagonist activity against *Listeria monocytogenes*.

17. An isolated bacterial strain belonging to genus *Enterococcus* and species *mundtii*, deposited on Jul. 17, 2008 under the accession number ATCC ® PTA-9382, wherein said strain are Gram-positive, lanceolate cocco, and exhibit antagonist activity against *Listeria monocytogenes*.

18. The method of claim 9, wherein said formulation comprises a cell concentration of the strains *C. maltaromaticum* ATCC® PTA-9380, *C. maltaromaticum* ATCC® PTA-9381 and *E. mundtii* ATCC® PTA-9382 of $10^7$-$10^9$ CFU/mL, each independently, and nisin at a concentration ranging from 500 to 5,000 IU/mL.

* * * * *